United States Patent [19]

Kuechler et al.

[11] Patent Number: 5,960,643
[45] Date of Patent: Oct. 5, 1999

[54] PRODUCTION OF ETHYLENE USING HIGH TEMPERATURE DEMETHANIZATION

[75] Inventors: Keith H. Kuechler, Friendswood; David R. Lumgair, Kingwood, both of Tex.

[73] Assignee: Exxon Chemical Patents Inc., Houston, Tex.

[21] Appl. No.: 08/880,973

[22] Filed: Jun. 23, 1997

Related U.S. Application Data

[60] Provisional application No. 60/034,240, Dec. 31, 1996, and provisional application No. 60/033,948, Dec. 31, 1996.

[51] Int. Cl.⁶ .................................................. F25J 3/02
[52] U.S. Cl. .................................. 62/620; 62/630; 62/935
[58] Field of Search ............................ 62/625, 628, 630, 62/635, 935, 620

[56] References Cited

U.S. PATENT DOCUMENTS

| | | |
|---|---|---|
| 3,055,183 | 9/1962 | Kniel . |
| 3,098,107 | 7/1963 | Becker . |
| 4,460,396 | 7/1984 | Kaiser et al. ............................... 62/630 |
| 4,464,189 | 8/1984 | Tedder ....................................... 62/628 |
| 4,720,293 | 1/1988 | Rowles et al. ............................. 62/630 |
| 5,678,424 | 10/1997 | Nazar ......................................... 62/630 |
| 5,811,621 | 9/1998 | Van Dijk . |

OTHER PUBLICATIONS

PCT/US97/23878 International Search Report.

*Primary Examiner*—Christopher B. Kilner
*Attorney, Agent, or Firm*—Bradley A. Keller

[57] ABSTRACT

This invention comprises a method of producing ethylene rich product streams from a pressurized charge gas mixture of olefins and other components received from olefin generation/preparation processes. The method of this invention may eliminate the need for cryogenic fractional distillation and other special separation equipment operating at temperatures below –55° F., and thus also potentially eliminate the refrigeration and heat exchange equipment needed to achieve those low temperatures. Alternatively, the method of this invention may eliminate the need for a circulating lean oil absorbant material, and thus also potentially eliminate the heat exchange equipment and reduces the refrigeration and fractional distillation load required to manage that material. In accordance with the process of this invention, a secondary ethylene rich product stream is produced at a rate and composition suitable for subsequent generation of a primary ethylene rich product potentially containing substantially no components having a boiling point at least as low as ethylene. Further, the secondary ethylene rich product stream may be suitable as feedstock in the production of ethylene derivatives, or be amenable to further concentration of ethylene using bulk separation techniques, or combinations thereof. Accordingly, the capital and operating cost associated with the manufacture of ethylene rich product streams from pressurized charge gas mixtures made by olefin generation processes may be significantly reduced through the method of this invention.

55 Claims, 5 Drawing Sheets

PRODUCTION OF ETHYLENE USING HIGH TEMPERATURE DEMETHANIZATION

This application claims priority to U.S. Provisional Pat. No. 60/034,240 and 60/033,948 filed Dec. 31, 1996.

FIELD OF INVENTION

This invention comprises a process for using pressurized charge gas mixtures of olefins, aliphatics, hydrogen, carbon monoxide, and other components, from a range of olefin generation/preparation techniques, to produce ethylene rich product streams suitable for use in the manufacture of ethylene bearing derivative products.

BACKGROUND OF THE INVENTION

Ethylene is the leading petrochemical in terms of production volume, sales value and number of derivatives. Total worldwide ethylene production in 1995 was estimated at 76 million tonne per year, expectations are for a growth rate of about 3% per year, and meeting this growth will require significant capital investment in new production facilities. Sales prices average on the order $440/tonne, translating to a worldwide cash volume for the ethylene business of over $30 billion per year. End and intermediate uses of ethylene include production of plastics, resins and fibers, and a host of other products.

Before ethylene can be sold or used, it is necessary to employ a process which recovers the ethylene component in a desireable, ethylene rich product stream by separating it from a myriad of other components, including methane, ethane, hydrogen and carbon monoxide, among others, all of which components are found together in a single stream obtained from another, different olefin generation/preparation process. Currently, a desireable, ethylene rich product stream is generally defined by those skilled in the art as one having greater than about 95 wt. % ethylene, containing substantially inert components such as methane and ethane in proportions less than about 2000 molar ppm each and potentially reactive components such as hydrogen, carbon monoxide, carbon dioxide, propylene and others in proportions less than about 20 molar ppm each. This definition arises from the nature of the derivative processes that use the ethylene rich product stream, each suffering varying degrees of adverse process performance and economic impact associated with the levels of the various non-ethylene components in the stream. Such material shall hereinafter be referred to as a primary ethylene rich product stream.

The recovery and separation process which produce s a primary ethylene rich product stream from components received from an olefin generation/preparation process represents the majority of total capital investment and energy usage required for ethylene manufacture. This reflects the difficulty associated with techniques required to manage the low normal boiling points and low relative volatilities of ethylene and the other components received from an olefin generation/preparation process. Furthermore, as recognized by those skilled in the art, capital recovery and energy usage are generally the two largest cost elements, respectively, in the total cost of ethylene manufacture. Thus, the process by which one effects recovery and separation to produce a primary ethylene rich product stream is a substantial factor in the economic feasibility of ethylene manufacture.

Methods for the recovery and separation of ethylene found in multi-component streams have been under consideration since the 1940's, when the first practical, large scale olefin generation technique of hydrocarbon pyrolysis, also called steam cracking, was developed and applied commercially. This olefin generation technique, now a substantially mature art, currently dominates the industry, utilizing a number of different hydrocarbon feedstocks. Also, alternative processes of potential commercial significance for the generation of olefins are emerging, such as the methanol to olefins process, taught in Kaiser, U.S. Pat. No. 4,499,327, and now being offered for commercial license by UOP. As shown in Table 1, olefin generation techniques of commercial importance, in general, create differing quantities of various byproduct components in a mixture with the desired ethylene component.

TABLE 1

Typical Component Distribution From Various Olefin Generation Techniques

| Process | Steam Cracking (1) | | | Methanol To Olefins |
| --- | --- | --- | --- | --- |
| Feedstock (excluding water) | Ethane ($C_2H_6$) | Light Naphtha (boiling range 95–300° F.) | Atmospheric Gas Oil (boiling range 365–635° F.) | (2) Methanol ($CH_3OH$) |
| Yields, wt. % (excluding water) | | | | |
| $H_2$ | 3.9 | 1.00 | 0.6 | 0.03 |
| CO | trac | trace | trac | 0.49 |
| $CO_2$ | trac | trace | trac | 2.46 |
| $CH_4$ | 3.8 | 18.00 | 11.2 | 1.45 |
| $C_2H_2$ | 0.4 | 0.95 | 0.4 | 0.00 |
| $C_2H_4$ | 53.0 | 34.30 | 26.5 | 53.73 |
| $C_2H_6$ | 35.0 | 3.80 | 3.4 | 1.67 |
| $C_3H_4$ | 0.0 | 1.02 | 0.8 | 0.00 |
| $C_3H_6$ | 0.8 | 14.10 | 13.4 | 26.37 |
| $C_3H_8$ | 0.1 | 0.35 | 0.2 | 1.53 |
| $C_4H_6$ | 1.1 | 4.45 | 5.0 | 0.00 |
| $C_4H_8$ | 0.1 | 3.70 | 3.7 | 6.64 |
| $C_4H_{10}$ | 0.2 | 0.10 | 0.1 | 1.21 |
| $C_5$ | 0.2 | 2.75 | 2.7 | 3.37 |
| $C_6$–$C_8$ | 0.3 | 1.20 | 1.2 | 0.88 |
| benzene | 0.3 | 6.90 | 6.9 | 0.00 |
| toluene | 0.0 | 3.20 | 3.2 | 0.00 |
| xylene + ethylbenzene | 0.0 | 1.30 | 1.3 | 0.00 |
| styrene | 0.0 | 0.79 | 0.7 | 0.00 |
| $C_9$–400° F. | 0.0 | 2.96 | 2.9 | 0.00 |
| fuel oil | 0.0 | 15.45 | 15.4 | 0.00 |
| carbon | trac | trace | trac | 0.17 |
| Total | 100.0 | 100.0 | 100.0 | 100.00 |

Note:
(1) per Howe-Grant, M. - Ed., Encyclopedia of Chemical Technology, fourth edition, Volume 9, page 880 (1994)
(2) per Nirula, S. C., Ethylene from Methane, Stanford Research Institute International Process Economics Program Report No. 208, page 4-2 (1994)

This mixture is generally unsuitable for further commercial use, hence the need for a distinct recovery and separation process. It should be stated that this is the case for many other olefin generation techniques not shown in Table 1, and for blends of mixtures from those techniques, one commercially important example being off-gas mixtures generated in various refinery processes blended with mixtures created in steam cracking. Further, such mixture may be a blend of those created by the olefin generation process and recycle streams from other parts of an ethylene manufacturing or ethylene derivative manufacturing facility, and may contain components other than those listed in Table 1.

The prevailing conventional wisdom relating to ethylene manufacture directs one, in addition to creating ethylene and byproduct components in a mixed stream via an olefin generation technique or blend of techniques, to further prepare that stream for introduction to the subsequent recovery and separation process. This may include, in various embodiments and sequences, the actions of cooling the stream from conditions at which the olefin generation reaction is effected to near ambient conditions, compressing the normally gaseous mixed stream to pressures usually between 200 and 600 psia, removing almost all of the water, carbon dioxide and sulfur compounds used or produced in the olefin generation step, and removing various normally liquid components at various pressures from the mixed stream. Hence the combination of steps described above, namely those of olefin generation and olefin preparation, embody what is referred to herein as the olefin generation/preparation process. Those skilled in the art recognize the result of employing an olefin generation/preparation process is production of a stream known as "charge gas," so named because it is both the mixed component gaseous charge to and from large and expensive compressors within the process, and the mixed component gaseous charge to the subsequent recovery and separation process. This latter stream will hereinafter be referred to as pressurized mixed olefin bearing charge gas.

Though methods for the recovery and separation of ethylene from a pressurized mixed olefin bearing charge gas are known, the low normal boiling points of ethylene and other components require the use of very low temperature vapor-liquid flash and fractional distillation techniques, in order to have a high recovery of the ethylene molecules present in a primary ethylene rich product stream, and thereby render ethylene manufacture sufficiently efficient for economic viability. Of particular expense in these processes are equipment items which serve to separate ethylene from lower boiling components such as hydrogen, carbon monoxide and methane. In current state of the art ethylene recovery and separation processes which dominate the industry, temperatures on the order of $-60$ to $-215°$ F. are typically employed in certain equipment items, requiring special metallurgies and refrigeration systems to effect, which represent a substantial portion of the total capital cost and energy consumption of ethylene manufacture. These are generally known to those skilled in the art as the chill train and the demethanizer tower, and a substantially dedicated refrigeration system needed to operate those equipment items at the requisite low temperatures, usually using ethylene as the refrigerant but sometime using methane and mixtures of light hydrocarbons, among other refrigerants. Also found in the recovery and separation process to produce an ethylene rich product stream are deethanizer and $C_2$ splitter fractional distillation towers, and reactors to eradicate the presence of acetylenes and dienes, along with heat exchangers, pumps and other supporting equipment items.

A less frequently practiced alternative to recovery and separation of ethylene from methane and lower boiling components using temperatures in the range of $-60$ to $-215°$ F. is comprised of employing a combined absorption and fractional distillation technique in the demethanizer tower, known to those familiar with the art as an absorber demethanizer. In this technique, a large volume of substantially ethylene free material of higher boiling point than ethylene, called lean oil, is introduced to the absorber demethanizer above the feed tray(s), usually the condenser drum or top tray, in the liquid state at about $-20$ to $-50°$ F. The dominant quantity of lean oil provides the bulk of the molecules in the vapor phase of the resulting overall vapor liquid equilibrium among all the components, and thus serves to force the bulk of the ethylene into the liquid phase, effectively absorbing it. The methane and lower boiling components, being more volatile, still tend to remain in the vapor phase, and thus over the course of numerous trays in the absorber demethanizer tower, separation of ethylene is effected as the lean oil with absorbed ethylene moves down the tower to the bottoms, and methane and lower boiling components move up the tower to the overhead. The absorber demethanizer has the potential advantage of eliminating the chill train, the substantially dedicated refrigeration system and some of the special metallurgies needed to operate at temperatures below $-55°$ F. However, with most types of pressurized mixed olefin bearing charge gas these advantages are offset by associated increases in high temperature refrigeration loads, energy consumption and cooling equipment items to manage the heat of absorption of ethylene in the lean oil within the absorber demethanizer. Further, additional size and energy consumption is required in subsequent distillation towers in the overall recovery and separation process to separate the large volume of lean oil from the desired ethylene and other byproduct components. For a representative example, see U.S. Pat. No. 5,019,143 granted to Mehra, et. al.

An advancing technology in the field of ethylene recovery and separation processes is that of non-distillative and non-cryogenic techniques, especially those that serve to separate olefins from non-olefins. One practical example is that of chemical absorption and desorption, such as the use of aqueous silver nitrate solutions in the British Petroleum "Selective Olefin Recovery" technology, described by Barchas in his conference presentation entitled *Olefin Recovery Via Chemical Absorption* and currently being offered for license by Stone and Webster, Inc., and which operates at ranges between about 600 psia/$70°$ F. and 2 psia/$400$ for absorption and desorption, respectively. Another is the use of membrane separators, such as described in U.S. Pat. No. 5,082,481 to Barchas, et. al. to remove approximately 20% of the hydrogen from a pressurized mixed olefin bearing charge gas prior to any refrigeration of the charge gas. These techniques have the advantage of a low capital cost per unit of ethylene processed, yet at present, they are incapable in and of themselves to transform a sufficient quantity of ethylene in the pressurized mixed olefin bearing charge gas into an ethylene rich product stream of sufficient purity for economic ethylene manufacture. They can be synergistically combined with flash and distillation equipment to produce some advantageous results, such as described in U.S. Pat. No. 5,452,581 to Dinh, et. al., wherein membranes are used to remove hydrogen in the chill train, thus saving energy by moving refrigeration load from the substantially dedicated low temperature refrigeration system to a high temperature refrigeration system. However, they cannot entirely eliminate the chill train, or low temperature refrigeration system, or fractional or absorptive distillation. Rather, their highest value seems to be in applications on relatively low volume secondary ethylene containing streams, such as process purges that are high in ethylene content in the case of chemical absorption. Hereinafter, such equipment and techniques shall be called bulk separation techniques.

Regardless of the specific embodiment of a recovery and separation process employed in ethylene manufacture, the vast majority of such processes are, in the conventional wisdom, directed to producing a single, primary ethylene rich product stream suitable for all possible end uses in the subsequent manufacture of ethylene derivatives. The dominance of processes producing a single, primary ethylene rich product stream is historically driven by polyethylene manufacture, which comprises the majority of the overall use of ethylene for derivative manufacture, and which has the most stringent specifications of all derivatives, usually requiring an ethylene rich product stream of high purity.

However, the prevailing conventional wisdom with respect to the composition requirements of the resultant primary ethylene rich product stream for derivative manufacture is just now being tested in the industry. In the Purvis conference presentation entitled *Cracker/Derivative Unit Integration*, there is discussed the recognition that many derivative processes do not require the historically high levels of ethylene purity required by that of polyethylene to function adequately. One such process is for ethylbenzene manufacture, as disclosed in U.S. Pat. No. 5,476,978 to Smith, et. al., which states the ethylene rich product stream used as feed may contain ethylene in concentrations as low as 5 wt. %, and such process as which is offered for license by CDTech, Inc. of Texas claims the ethylene rich product stream may contain appreciable levels of hydrogen and carbon monoxide. Another derivative process is that for aldehyde, alcohol, or ester manufacture, as described in European Patent Application serial number PCT/EP96/00361 by Kiss, et. al., wherein suitable feeds include an ethylene rich product stream that need contain only between 30 and 75 wt. % ethylene, and which may contain appreciable quantities of hydrogen and carbon monoxide. Further, the question of the purity of a primary ethylene rich product stream for use in polyethylene manufacture itself is being broached, with concentrations of ethylene as low as 85% being discussed. The reason for entertaining the production and application of a primary ethylene rich product stream lower in ethylene content than historically prevalent is to allow reductions the capital and energy requirements associated with producing the primary ethylene rich product stream, and ultimately provide reductions to the cost of the ethylene bearing derivative product.

Yet, in the face of the changing requirements for primary ethylene rich product streams for the manufacture of various derivatives, almost all current teachings in patents and open literature continue to direct one to make a single, primary ethylene rich product stream from the recovery and separation process. Those few items that refer to a different, secondary ethylene rich product stream teach of the stream emanating from the deethanizer fractional distillation tower to save additional load on the $C_2$ splitter tower. As far as applicant is aware, it is heretofore unknown to use a demethanizer tower to supply as an overhead a secondary ethylene rich product stream for potential use in certain derivative processes, or for feed to advantageous applications of the advancing art in low cost non-distillative and non-cryogenic separation techniques, while continuing to supply a primary ethylene rich product stream with more stringent composition requirements for other derivatives, and simultaneously reducing capital costs and energy requirements for the overall separation and recovery process, potentially eliminating the chill train and dedicated low temperature refrigeration system, or alternatively potentially eliminating the circulation and management of lean oil to the demethanizer tower.

SUMMARY OF THE INVENTION

This invention comprises a method of producing ethylene rich product streams from a pressurized charge gas mixture of olefins, aliphatics, carbon monoxide and hydrogen made by olefin generation/preparation processes. The condensor temperature of the demethanizer tower within the overall olefin recovery/separation facilities is increased over standard operating levels currently accepted as state of the art, namely above about −140° F. In a preferred embodiment, the method of this invention eliminates the need for cryogenic fractional distillation and other special separation equipment operating at temperatures below about −55° F., and thus also eliminates the refrigeration and heat exchange equipment needed to achieve those low temperatures. Alternatively, in another preferred embodiment the method of this invention eliminates the need for a circulating lean oil absorbant material, and thus also eliminates the heat exchange equipment and reduces the refrigeration and fractional distillation load required to manage that material. In accordance with the process of this invention, a secondary ethylene rich product stream may be produced as the overhead of a distillation column at a rate and composition suitable for subsequent generation of a primary ethylene rich product substantially free of components with a boiling point at least as low as ethylene. Further, the secondary ethylene rich product stream may be suitable as feedstock in the production of ethylene derivatives, or be amenable to further concentration of ethylene using bulk separation techniques or combinations thereof. Accordingly, the capital and operating cost associated with the manufacture of ethylene rich product streams from pressurized charge gas mixtures made by olefin generation processes is significantly reduced through the method of this invention.

The process of this invention comprises introducing a pressurized mixed olefin bearing charge gas to an olefin recovery/separation facility operating to perform at least the function of demethanization, where within such facilities bulk separation devices may or may not be inserted to modify process stream compositions, operating the demethanizer column to produce a secondary ethylene rich product stream as the overhead, and a bottoms stream balance; subsequently making a primary ethylene rich product stream from said bottoms balance; possibly providing the secondary ethylene rich product stream as feedstock for derivative manufacture or combusted for disposal or the generation of useful heat. In a preferred embodiment, the secondary ethylene rich product stream will contain substantially all of the input components of a boiling point at least as low as ethylene. In another preferred embodiment, the demethanizer tower operates with a condensor temperature of above about −55 in the absence of lean oil absorption, within an olefin separation and recovery facility absent a chill train.

DETAILED DESCRIPTION OF THE INVENTION

Figure 1A:
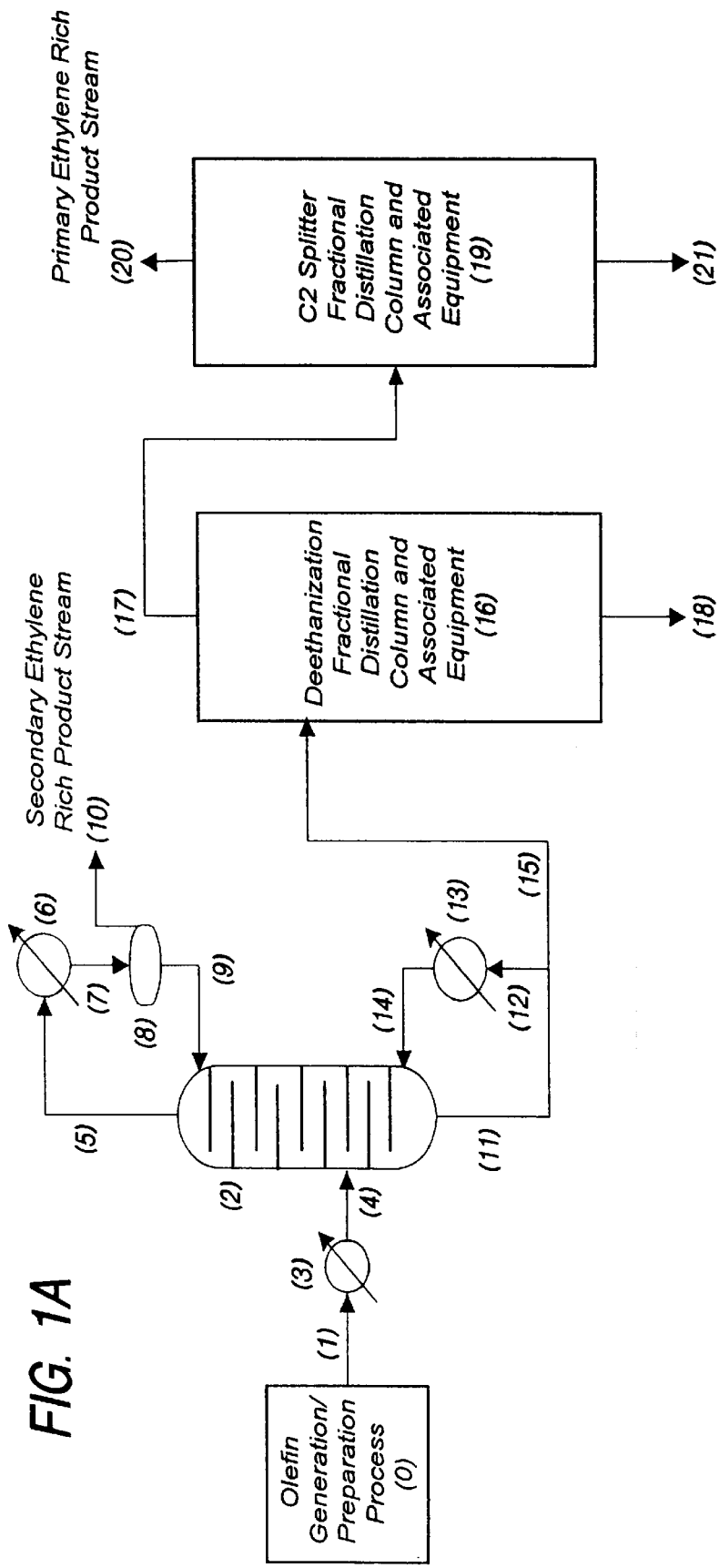
FIG. 1A is a schematic diagram of the olefin separation and recovery facilities of an ethylene plant using a preferred embodiment of the present invention, showing production of a secondary ethylene rich product stream from a demethanizer fractional distillation column which is the first column in the overall series of columns, followed by a deethanizer, and a $C_2$ splitter producing as the overhead a primary ethylene rich product stream.

Referring to FIG. 1A, an olefin generation/preparation process (0) creates a pressurized mixed olefin bearing charge gas (1) that is fed to a demethanizer fractional distillation column (2) at a pressure between about 200 and 800 psia, and preferably in the range from about 400 to 620 psia which is converted to be the optimum among process (0) based upon capital and energy requirements for compression and the eventual composition of the resultant secondary ethylene rich product stream discussed below. In this embodiment, the charge gas is cooled to a temperature of no lower than −55° F., in heat exchange equipment (3) prior to entering the feed tray of the demethanizer column as stream (4). Within the demethanizer column fractional distillation takes place among multiple trays, ultimately resulting in a vapor stream (5) entering the overhead condenser (6). In the overhead condenser, heat is removed from the input vapor until material exiting the condenser (7) is partially condensed against a refrigerant to a temperature of between about 0 and no lower than −55° F. in the range of from about −20 to −50° F., as an optimum among condensor heat transfer area, refrigerant system energy requirements and the resultant composition of secondary ethylene rich product discussed below. Stream (7) is then introduced to a drum (8), or other such vapor-liquid separation device. A liquid stream (9) is created and returned to the demethanizer column as reflux to facilitate fractional distillation, and note that no lean oil is introduced to the demethanizer column at this or any other point. Further, a vapor stream (10) is manifested as a secondary ethylene rich product stream, containing mostly ethylene and virtually all of the input components of a lower boiling point than ethylene, including hydrogen, carbon monoxide and methane, and very little of the components of a higher boiling point than ethylene.

Said demethanizer column also manifests a liquid bottoms stream (11), a portion of which (12) is introduced to the column reboiler (13) wherein heat is input to create a mixed vapor-liquid stream (14) which is returned to the column to facilitate fractional distillation. The remainder is withdrawn from the demethanizer column as a liquid bottoms product (15), comprising the balance of the input ethylene and higher boiling components and virtually none of the components of a lower boiling point than ethylene.

The proportion of ethylene in the secondary ethylene rich product stream relative to that in the pressurized mixed olefin bearing charge gas is predominantly a function of the ratio of ethylene to hydrogen, ethylene to carbon monoxide and ethylene to methane in the charge gas, and the operating pressure and temperature of the demethanizer condenser. The latter parameters establish the vapor-liquid equilibrium composition set determined by the laws of nature in drum (8), and the former component ratios establish the material balance required achieve that equilibrium composition set and hence the rate of stream (10). In a preferred embodiment of the present invention, an olefin generation/preparation process (0) will be selected that inherently creates, without the need for bulk separation devices, a pressurized mixed olefin bearing charge gas with a very high ratio of ethylene to hydrogen, ethylene to carbon monoxide and ethylene to methane, such as Methanol To Olefins, or catalytic cracking of hydrocarbons as described in PCT WO 96/16004, Application no. PCT/US95/15281 applicants Mohr, et. al., most preferably Methanol To Olefins. Table 2 defines the compositions and rates of the secondary ethylene rich product stream that will result from a given composition and rate of charge gas that may contain hydrogen, carbon monoxide or methane in various ratios with ethylene.

TABLE 2

Compositions and Rates of Secondary Ethylene Rich Product Stream from Demethanizer Overhead at Various Feed Compositions and Condensor Conditions
BASIS: $C_2H_4$ with a single lower boiling component to demethanizer feed Stream (1) in FIG. 1A

| | Condensor Conditions | | | | | |
|---|---|---|---|---|---|---|
| Pres. (psia) | | 450 | | | 600 | |
| Temp. (° F.) | −20 | −35 | −50 | −20 | −35 | −50 |
| Lower Boiling Component in Feed Stream | Rate and Proportion of Ethylene in Secondary Ethylene Rich Product Stream | | | | | |
| Hydrogen ($H_2$) | | | | | | |
| mol % $C_2H_4$ in Secondary Ethylene Rich Product | 74 | 61 | 48 | 60 | 49 | 39 |
| lb. $C_2H_4$ in Secondary Ethylene Rich Product per lb. $H_2$ in Feed Stream | 39.2 | 21.4 | 13.0 | 21.1 | 13.3 | 8.8 |
| Carbon Monoxide (CO) | | | | | | |
| mol % $C_2H_4$ in Secondary Ethylene Rich Product | 74 | 61 | 49 | 61 | 51 | 41 |
| lb. $C_2H_4$ in Secondary Ethylene Rich Product per lb. CO in Feed Stream | 27.9 | 15.6 | 9.8 | 1.6 | 1.0 | 0.7 |
| Methane ($CH_4$) | | | | | | |
| mol % $C_2H_4$ in Secondary Ethylene Rich Product | 69 | 55 | 43 | 68 | 43 | 34 |
| lb. $C_2H_4$ in Secondary Ethylene Rich Product per lb. $CH_4$ in Feed Stream | 3.8 | 2.1 | 1.3 | 1.9 | 1.1 | 0.9 |

Note: As compiled using the PRO/II chemical simulation program, by Simulation Sciences, Inc. of California, utilizing the Soave-Redlich-Kwong equation of state, assuming at least five theoretical plates above the topmost feed tray.

As long as the ratio of ethylene to the lower boiler component exceeds that listed in Table 2, it is possible to create a secondary ethylene rich product stream as the overhead of the demethanizer and have ethylene remaining in the bottoms stream with which to subsequently create a primary ethylene rich product stream. The presence in the demethanizer feed of components with a higher boiling point than ethylene will have only a minor impact on the data shown in Table 2, given that the number of fractional distillation plates, feed location among those plates and reboiler and condenser duties, in any case, are chosen to effect a separation resulting in the overwhelming proportion of those components leaving the demethanizer in the bottoms stream. This is generally the chosen mode of operation because of the presence of propylene in the demethanizer feed, as while various ethylene derivative processes can tolerate hydrogen and inserts, they may not tolerate other olefin species well, and the propylene has economic value in its own right. However, to the extent that components of a higher boiling point than ethylene are present in the secondary ethylene rich product stream, particularly ethane if present in large enough proportions in the feed to the demethanizer, the concentration of ethylene in the stream and the proportion of ethylene relative to lower boiling component will be reduced from the figures shown in Table 2, without changing the nature of this invention.

The impact of the level of low boiling components are approximately additive. If hydrogen, carbon monoxide and methane are all present in the demethanizer feed along with ethylene, the rate of ethylene in the secondary ethylene rich product stream would be approximately the sum of the independent proportions listed in Table 2. The composition of the stream would be approximately the weight average of the independent compositions listed in Table 2.

In one embodiment, given certain economic circumstances and a relatively low rate of the secondary ethylene rich product stream, it may be desireable to simply combust this stream for disposal or the generation of useful heat.

Returning to FIG. 1A, the demethanizer bottoms stream (15) is introduced to a deethanizer fractional distillation column (16). In this column, via techniques well known in the art, is produced an overhead stream (17) containing substantially all of the input ethylene and very little of the components of a higher boiling point than ethane, and a bottoms stream (18) containing very little ethylene among the balance of the input components.

The deethanizer overhead stream (17) is then sent to a $C_2$ splitter fractional distillation column(19), where using techniques well established in the art, an overhead stream (20) is produced containing virtually all of the input ethylene and very little ethane, which is the primary ethylene rich product stream of the overall process of this invention. Also produced is a bottoms product (21) comprised of very little ethylene and most all of the input ethane and higher boiling components.

Figure 1B:
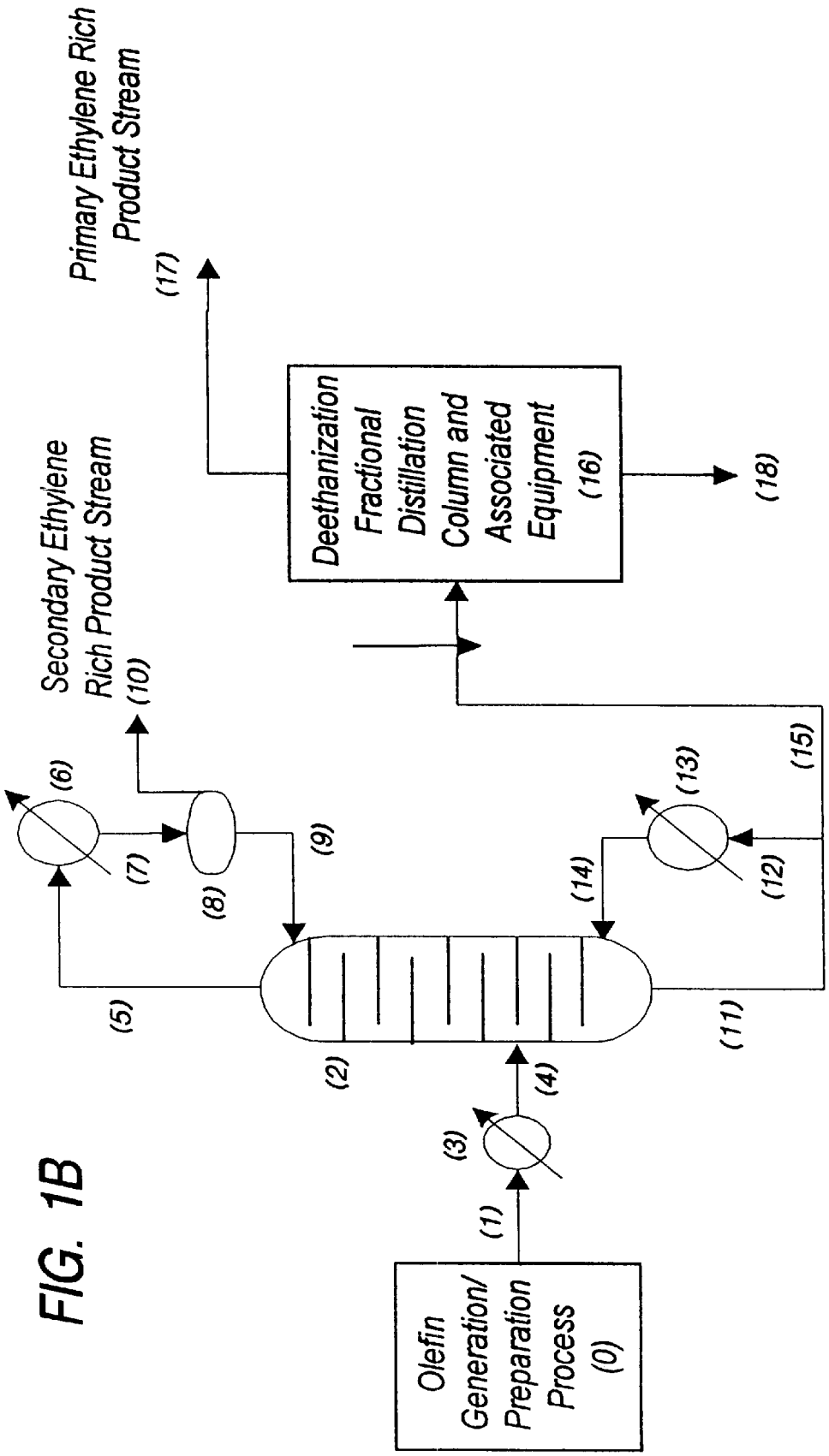
FIG. 1B is a schematic diagram of the olefin separation and recovery process of an ethylene plant using a preferred embodiment of the present invention showing production of a secondary ethylene rich product stream from a demethanizer fractional distillation column which is the first column in the overall series of columns, followed by a deethanizer producing as the overhead a primary ethylene rich product stream.
Figure 1C:
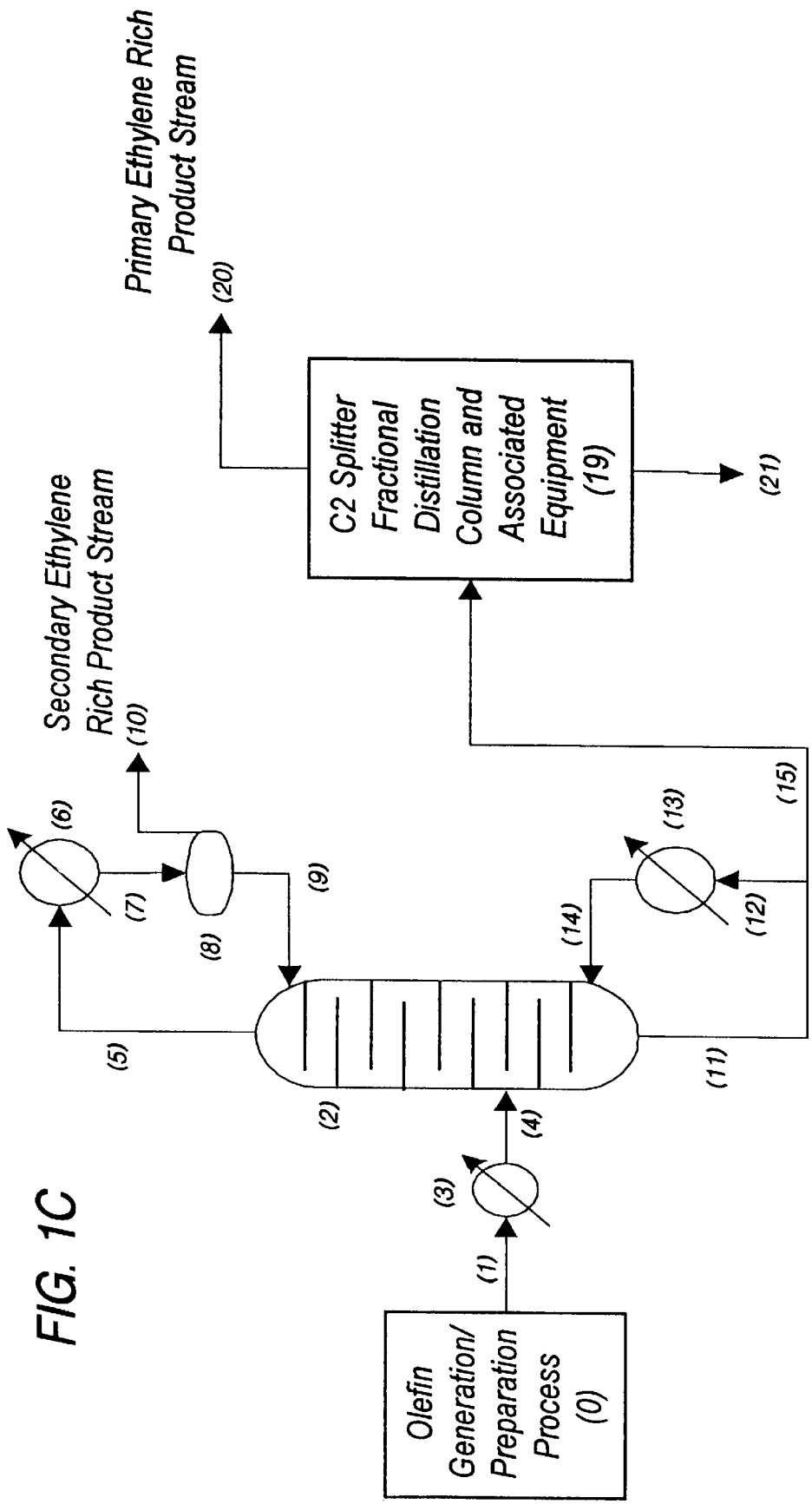
FIG. 1C is a schematic diagram of the olefin separation and recovery process of an ethylene plant using a preferred embodiment of the present invention showing production of a secondary ethylene rich product stream from a demethanizer fractional distillation column which is the first in the overall series of columns, followed by a $C_2$ splitter producing as the overhead a primary ethylene rich product stream.
Figure 1D:
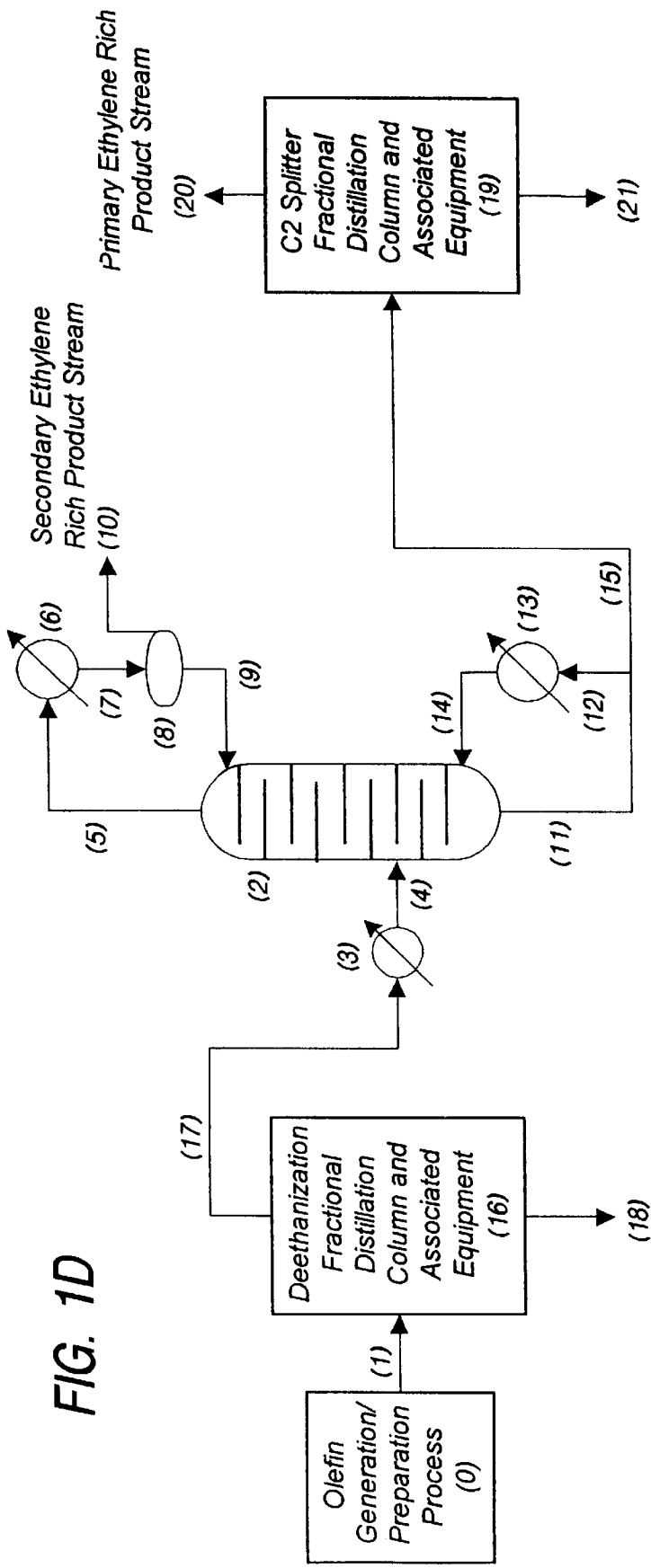
FIG. 1D is a schematic diagram of the olefin separation and recovery process of an ethylene plant using a preferred embodiment of the present invention showing production of a secondary ethylene rich product stream from a demethanizer fractional distillation column which is the second in the overall series of columns, preceded by a deethanizer column and followed by a $C_2$ splitter column.

Additional embodiments of the instant invention are shown in FIGS. 1B, 1C and 1D. In these figures the sequence of fractional distillation columns are changed or certain columns are eliminated. Such permutations of column sequence are common in the industry, known to those skilled in the art as "deethanizer first," "depropanizer first," etc., referring to the initial distillation operation performed in the overall sequence, and chosen based on energy and capital optimizations associated with the specific type of charge gas produced in the olefin generation/preparation step (0). Regardless of the column sequence, the impact of the present invention is the same. In a preferred embodiment, the demethanizer column is operated with a condenser temperature above about −55° F., and a secondary ethylene rich product is produced as the overhead, allowing subsequent production of a primary ethylene rich product without the use of a substantially dedicated refrigeration system, lean oil circulation, or a chill train.

Figure 2:
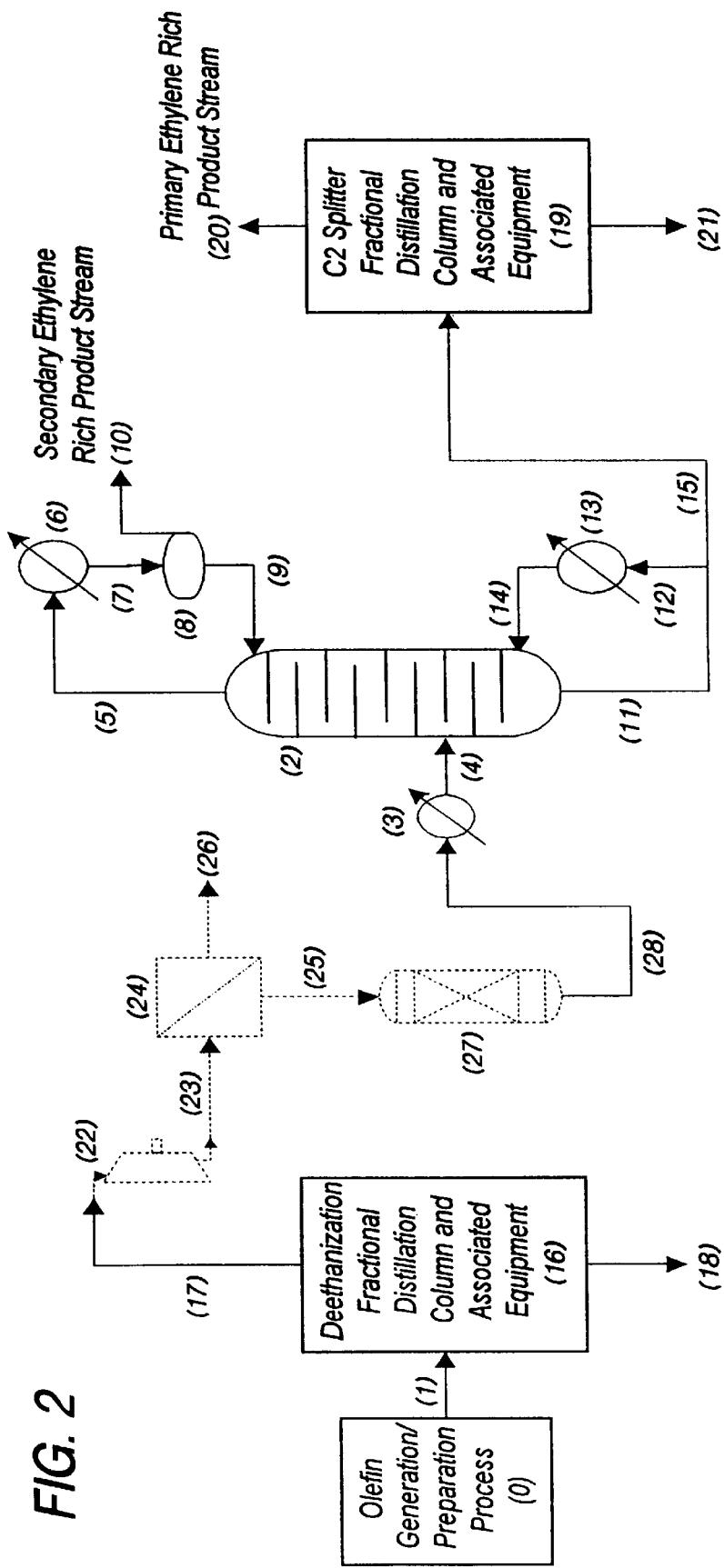
FIG. 2 is a modification of FIG. 1D, wherein dotted lines are used to denote the potential presence of various equipment items in the present invention as optional embodiments, as a sample of how such various equipment items may be used with the series of fractional distillation columns in any order or sequence.

Further additional embodiments of the present invention are shown in FIG. 2. This figure represents a modification of FIG. 1A, wherein various equipment items known to those skilled in the art are shown in dotted lines interspersed in logical parts of the overall separation and recovery process specified by this invention. An item of particular note is a non-cryogenic, non-distillative bulk separation process (21) installed at so prior to the demethanizer, which serves to remove a portion of the low boiling components in the charge gas as stream (22), leaving a stream reduced in components of a lower boiling point than ethylene as feed (23) to the demethanizer column. Some bulk separation items are well known to industry, including commercial applications like hollow fiber membranes offered by MEDAL Limited Partnership as described by Fleming and Dupuis in their article *Hydrogen Membrane Recovery Estimates*, or the chemical absorption technique called "Selective Olefin Recovery" noted above. Another technique is a reactive removal of hydrogen and carbon monoxide as described in U.S. Patent Application Attorney Docket Number 96B082, by Ou, et. al. In modifying the ratio of low boiling components to ethylene in the feed to the demethanizer in the instant invention, one can modify the rate and composition of the secondary ethylene rich product stream in accordance with the information provided in Table 2. In addition, one may use such techniques on the secondary ethylene rich product stream to reduce the quantity of low boiling components contained therein (24), potentially increasing its economic value to a derivative unit, and providing a stream rich in components of a lower boiling point than ethylene, which may have economic value in its own right.

Further, in FIG. 2, there may be present a host of equipment items to serve a variety of purposes. One such item (25) performs a reactive conversion of acetylene to ethylene and ethane in the presence of hydrogen, known to those skilled in the art as an acetylene converter. Such a technique will eliminate the presence of acetylene in either the secondary or primary ethylene rich product stream, or both, depending on where in the overall recovery and separation process it is located.

In accordance with the method of this invention, such ancillary equipment items of the type and purpose noted in the description of FIG. 2 can be located in any logical place in the overall recovery and separation process, for any sequence of fractional distillation columns, and still achieve the benefits of utilizing the instant invention, and hence are included within the scope of the instant invention. This includes the use of stages of compression usually found in the olefin generation/preparation process, but sometimes placed in between columns on various overhead streams to optimize between compression energy requirements and piping required to move the streams around among the various equipment items, and pumps used to move streams among the various equipment items or modify the pressure of the streams to and from those equipment items. Further, in less preferred but still useful embodiments, a chill train, lean oil or temperatures below about −55 may be employed, but at temperatures above those currently used in the conventional wisdom, or the demethanizer may be operated to retain appreciable quantities of components of a boiling point at least as low as ethylene, saving varying amounts of energy and capital while providing further flexibility in controlling the rate of the secondary ethylene product stream in accordance with the desired requirements for the primary ethylene rich product stream.

The invention is illustrated but not limited by the examples which follow. In each of the following examples a feed rate of 100,000 pounds per hour of ethylene contained in the charge gas from an olefin generation/preparation process (0) is assumed. The quantity of other components is thus defined by the overall stream composition listed in each example.

EXAMPLE 1 —DEMETHANIZER FIRST ON UNADULTERATED CHARGE GAS

Referring to FIG. 1, A Methanol To Olefins olefin generation/preparation process (0) creates a mixed olefin bearing charge gas (1) with a composition reflected by that given in Table 1 upon having all of the carbon dioxide and carbon removed, as shown in Table 3, and a pressure of 610 psia and a temperature of 90° F.:

TABLE 3

Composition of Mixed Olefin Bearing Charge Gas (1) for Example 1

| Component | Wt. % |
|---|---|
| $H_2$ | 0.03 |
| CO | 0.50 |
| $CH_4$ | 1.49 |
| $C_2H_4$ | 55.18 |
| $C_2H_6$ | 1.72 |
| $C_3+$ | 41.08 |
| Total | 100.00 |

The charge gas is taken through heat exchanger (3), where heat is removed to provide feed to the demethanizer (2) at a temperature of 0° F., and a pressure drop of 8 psia is incurred. The demethanizer, with the equivalent of 30 theoretical plates and the feed on the eighth tray from the bottom is operated with a temperature in drum (8) of −50° F. and a pressure of 600 psia, with a reboiler and condenser duty sufficient to provide a quantity of propylene in the secondary ethylene rich product stream (10) of 10 mol ppm. As derived from Table 2, the quantity and composition of the secondary ethylene rich product stream will be approximately as shown in Table 4, containing all of the hydrogen, carbon monoxide and methane in the charge gas:

TABLE 4

Composition of Secondary Ethylene Rich Product Stream (10) for Example 1

| Component | Mol % | Lb-mol/hr | Wt. % | Lb/hr. |
|---|---|---|---|---|
| $H_2$ | 7.62 | 27.0 | 0.75 | 54 |
| CO | 9.14 | 32.4 | 12.59 | 906 |
| $CH_4$ | 47.63 | 168.8 | 37.53 | 2,700 |
| $C_2H_4$ | 35.27 | 125.00 | 48.64 | 3,500 |
| $C_2H_6$ | 0.34 | 1.2 | 0.49 | 35 |
| $C_3+$ | — | — | — | trace |
| Total | 100.00 | 354.4 | 100.00 | 7,195 |

The demethanizer bottoms product stream (15) is fed to deethanizer column (16), which is supplied with sufficient trays, reboiler duty and condenser duty to effect a fractional distillation separation between ethane and propylene, wherein there is contained in the overhead product (17) only 100 wt ppm propylene and virtually all of the input ethylene, and there is contained in the bottoms product (18) about 100 wt ppm ethane and all of the input components of a higher boiling point.

The deethanizer overhead (17) is sent to a $C_2$ splitter column (19), which is supplied with sufficient trays, reboiler duty and condenser duty to effect a fractional distillation separation between ethylene and ethane, wherein there is contained in the overhead product (20) virtually all of the input ethylene and only 500 mol ppm ethane and virtually no hydrogen, carbon monoxide or methane originally present in the charge gas. Stream (20) constitutes the primary ethylene rich product stream currently established by industry as the standard for merchant markets.

EXAMPLE 2 —DEETHANIZER FIRST UTILIZING BULK SEPARATION BEFORE DEMETHANIZATION

Please refer to FIG. 2. A Ethane Steam Cracking olefin generation/preparation process (0) creates a mixed olefin bearing charge gas (1) with a composition reflected by that given in Table 1 upon having all of the carbon dioxide, carbon and most of the C7+ molecules removed, as shown in Table 5, at a pressure of 400 psia and a temperature of 90° F.:

TABLE 5

Composition of Mixed Olefin Bearing Charge Gas (1) for Example 2

| Component | Wt. % |
|---|---|
| $H_2$ | 3.94 |
| CO | trace |
| $CH_4$ | 3.83 |
| $C_2H_2$ | 0.43 |
| $C_2H_4$ | 53.14 |
| $C_2H_6$ | 35.09 |
| $C_3+$ | 3.57 |
| Total | 100.00 |

The charge is introduced to deethanizer column (16), which is supplied with sufficient trays, reboiler duty and condenser duty to effect a fractional distillation separation between ethane and propylene, wherein there is contained in the overhead product (17) only 100 wt ppm propylene and virtually all of the input ethylene, and there is contained in the bottoms product (18) about 100 wt ppm ethane and all of the input components of a higher boiling point. The deethanizer column step has introduced a pressure drop of 10 psia, and the pressure of stream (17) is now 390 psia.

The deethanizer overhead (17) is taken through a compressor (22) where the pressure is increased to 620 psia at point (23), and introduced to a commercial MEDAL hollow fiber membrane (24) designed and operated to effect a removal of 60% of the hydrogen to create retentate stream (25), whose composition is shown in Table 6, and whose pressure is now 470 psi. Also created is stream (26) as the permeate, comprised of the targeted hydrogen plus some bypass methane, acetylene and ethylene removed from stream (23).

TABLE 6

Composition of Stream (25) from Bulk Separation Device (24) in Example 2

| Component | Wt. % | Lb/hr. |
|---|---|---|
| $H_2$ | 1.69 | 2,966 |
| CO | — | trace |
| $CH_4$ | 3.95 | 6,919 |
| $C_2H_2$ | 0.45 | 793 |
| $C_2H_4$ | 56.45 | 99,000 |
| $C_2H_6$ | 37.46 | 65,703 |
| $C_3+$ | — | trace |
| Total | 100.00 | 175,381 |

Stream (25) is introduced to an acetylene converter reactor (27), designed and operated to destroy all of the acetylene with 70% converted to ethylene and 30% converted to ethane via stoichiometric reaction with the hydrogen in the stream. The result is stream (28), which is taken through heat exchanger (3), where heat is removed to provide feed to the demethanizer (2) at a temperature of 0° F., whose composition and rate are given in Table 7. Through items (27) and (3), a pressure drop of 18 psi is incurred. The demethanizer, with the equivalent of 20 theoretical plates and the feed on the eighth tray from the bottom is operated with a condenser temperature in drum (8) of −35° F. and a pressure of 450 psia, with a reboiler and condenser duty sufficient to provide a quantity of methane in the demethanizer bottoms product stream (15) of 135 mol ppm. In this instance, due to the relatively high ratio of ethane to ethylene in the demethanizer feed, ethane is allowed in secondary ethylene rich product stream (10) as a potential optimum between refrigeration requirements on condenser (6) and recovery of ethylene in the bottoms product stream (15) for subsequent manufacture of the primary ethylene rich product stream. Thus, as discussed above, the rate and proportion of ethylene in the secondary ethylene rich product stream (10) will be somewhat lower than predicted by Table 2, while still containing all of the hydrogen, carbon monoxide and methane in the charge gas, as shown in Table 8:

TABLE 7

Composition of Stream (4) Feed to Demethanizer Column in Example 2

| Component | Wt. % | Lb/hr. |
|---|---|---|
| $H_2$ | 1.65 | 2,887 |
| CO | — | trace |
| $CH_4$ | 3.95 | 6,919 |
| $C_2H_2$ | — | 0 |
| $C_2H_4$ | 56.79 | 99,598 |
| $C_2H_6$ | 37.61 | 65,977 |
| $C_3+$ | — | trace |
| Total | 100.00 | 175,381 |

TABLE 8

Composition of Secondary Ethylene Rich Product Stream (10) for Example 2

| Component | Mol % | Lb-mol/hr | Wt. % | Lb/hr. |
|---|---|---|---|---|
| $H_2$ | 34.45 | 1443.5 | 3.84 | 2,887 |
| CO | trace | trace | trace | trace |
| $CH_4$ | 10.31 | 432.0 | 9.19 | 6,912 |
| $C_2H_4$ | 47.85 | 2,005.0 | 74.63 | 56,140 |
| $C_2H_6$ | 7.39 | 309.4 | 12.34 | 9,283 |
| $C_3+$ | — | — | — | — |
| Total | 100.00 | 4,189.9 | 100.00 | 75,222 |

The demethanizer bottoms product stream (15) is sent to a $C_2$ splitter column (19), which is supplied with sufficient trays, reboiler duty and condenser duty to effect a fractional distillation separation between ethylene and ethane, wherein there is contained in the overhead product (20) virtually all of the input ethylene and only 500 mol ppm ethane and virtually no hydrogen, carbon monoxide or methane originally present in the charge gas. Stream (20) constitutes the primary ethylene rich product stream currently established by industry as the standard for merchant markets.

As one can see from these examples, the advantages of the present invention include being able to achieve the same results, with substantially less capital equipment.

The invention has been described with reference to its preferred embodiments. In view of this description, one skilled in the art will appreciate changes and modifications which may be made that do not depart from the scope and spirit of the invention as described above and claimed hereafter.

We claim:

1. A process for producing an overhead comprising a secondary ethylene rich product stream from a pressurized mixed olefin bearing charge gas comprising introducing said charge gas directly to a high temperature demethanizer fractional distillation tower contained in an overall olefin recovery and separation facility, under conditions on said demethanizer effective to produce a remaining bottoms stream containing some ethylene present in said charge gas and eventually recovering a primary ethylene rich product stream from said bottoms stream, wherein said conditions comprise a condenser temperature sufficiently high to eliminate the need for a chill train.

2. The process of claim 1 where said overall olefin recovery and separation facility contains non-distillative separation or reaction transformation techniques to modify the content of acetylenes, dienes, or components of a lower boiling point than ethylene on any stream, potentially including the secondary rich ethylene product stream.

3. The process of claim 1 wherein:
said secondary ethylene rich product stream consists mostly of ethylene and substantially all of the components in the feed to said fractional distillation tower having a boiling point at least as low ethylene; and,
said bottoms stream consists of ethylene and components in the feed to said fractional distillation tower having a boiling point at least as high as ethylene.

4. The process of claim 2 wherein:
said secondary ethylene rich product stream consists mostly of ethylene and substantially all of the components in the feed to said fractional distillation tower having a boiling point at least as low ethylene; and,
said bottoms stream consists of ethylene and components in the feed to said fractional distillation tower having a boiling point at least as high as ethylene.

5. The process of claim 3 wherein said conditions comprise a condenser temperature of no lower than about −55° F.

6. The process of claim 4 wherein said conditions comprise a condenser temperature of no lower than about −55° F.

7. The process of claim 5 wherein said ethylene rich product streams are produced in the absence of absorption by lean oil, and in the absence of a chill train.

8. The process of claim 6 wherein said ethylene rich product streams are produced in the absence of absorption by lean oil, and in the absence of a chill train.

9. The process of claim 7 where the pressurized mixed olefin bearing charge gas is obtained from the methanol to olefins reaction.

10. The process of claim 8 where the pressurized mixed olefin bearing charge gas is obtained from the methanol to olefins reaction.

11. The process of claim 7 where the pressurized mixed olefin bearing charge gas is obtained from the pyrolysis or catalytic cracking of hydrocarbon feedstocks.

12. The process of claim 8 where the pressurized mixed olefin bearing charge gas is obtained from the pyrolysis or catalytic cracking of hydrocarbon feedstocks.

13. The process of claim 9 wherein all or part of said secondary ethylene rich product stream is eventually combusted for disposal or the generation of useful heat.

14. The process of claim 10 wherein all or part of said secondary ethylene rich product stream or said modified secondary ethylene rich product stream is eventually combusted for disposal or the generation of useful heat.

15. The process of claim 11 wherein all or part of said secondary rich ethylene product stream is eventually combusted for disposal or the generation of useful heat.

16. The process of claim 12 wherein all or part of said secondary ethylene rich product stream or said modified secondary ethylene rich product stream is eventually combusted for disposal or the generation of useful heat.

17. The process of claim 9 wherein all or part of said secondary ethylene rich product stream is introduced to another process that serves to transform the olefins in that stream to other products through a reaction.

18. The process of claim 10 wherein all or part of said secondary ethylene rich product stream or said modified secondary ethylene rich product stream is introduced to another process that serves to transform the olefins in that stream to other products through a reaction.

19. The process of claim 11 wherein all or part of said secondary ethylene rich product stream is introduced to another process that serves to transform the olefins in that stream to other products through a reaction.

20. The process of claim 12 wherein all or part of said secondary ethylene rich product stream or said modified ethylene rich product stream is introduced to another process that serves to transform the olefins in that stream to other products through a reaction.

21. The process of claim 17 where said reaction is hydroformylation and said other products are aldehydes or alcohols.

22. The process of claim 18 where said reaction is hydroformylation and said other products are aldehydes or alcohols.

23. The process of claim 19 where said reaction is hydroformylation and said other products are aldehydes or alcohols.

24. The process of claim 20 where said reaction is hydroformylation and said other products are aldehydes or alcohols.

25. The process of claim 17 where said another process is the manufacture of acetic acid, linear alpha olefins, acetaldehyde, vinyl acetate monomer, vinyl chloride monomer, ethanol, ethylbenzene, or polyethylene.

26. The process of claim 18 where said another process is the manufacture of acetic acid, linear alpha olefins, acetaldehyde, vinyl acetate monomer, vinyl chloride monomer, ethanol, ethylbenzene, or polyethylene.

27. The process of claim 19 where said another process is the manufacture of acetic acid, linear alpha olefins, acetaldehyde, vinyl acetate monomer, vinyl chloride monomer, ethanol, ethylbenzene, or polyethylene.

28. The process of claim 20 where said another process is the manufacture of acetic acid, linear alpha olefins, acetaldehyde, vinyl acetate monomer, vinyl chloride monomer, ethanol, ethylbenzene, or polyethylene.

29. A method for producing an overhead comprising a secondary ethylene rich product stream from a mixed charge gas comprising introducing said charge gas directly to a high temperature demethanizer fractional distillation tower, separating said mixed charge gas into a bottoms and said overhead under conditions in said demethanizer effective to produce said overhead, said conditions comprising a temperature sufficiently low to eliminate the need for a chill train.

30. The method of claim 29 wherein said conditions comprise a temperature of about −55° F. (−48° C.) or higher.

31. The method of claim 29 wherein:
said overhead consists essentially of ethylene and components of said mixed charge gas having a boiling point at least as low as ethylene; and,
said bottoms consists essentially of ethylene and components of said mixed charge gas having a boiling point at least as high as ethylene.

32. The method of claim 30 wherein:
said overhead consists essentially of ethylene and components of said mixed charge gas having a boiling point at least as low as ethylene- and,
said bottoms consists essentially of ethylene and components of said mixed charge gas having a boiling point at least high as ethylene.

33. The method of claim 29 wherein said first ethylene rich product stream is produced in the absence of absorption by lean oil, and in the absence of a chill train.

34. The method of claim 31 wherein said first ethylene rich product stream is produced in the absence of absorption by lean oil, and in the absence of a chill train.

35. The method of claim 32 wherein said first ethylene rich product stream is produced in the absence of absorption by lean oil, and in the absence of a chill train.

36. The method of claim 29 wherein said mixed charge gas comprises at amount of ethylene, and said secondary ethylene rich product stream comprises between about 1–50% of said total amount of ethylene.

37. The method of claim 30 wherein said mixed charge gas comprises a total amount amount of ethylene, and said secondary ethylene rich product stream comprises between about 1–50% of said total amount of ethylene.

38. A method for producing a secondary ethylene rich product stream from a mixed charge gas comprising:
introducing a pressurized mixed olefin bearing charge gas into a demethanizer;
separating said mixed charge gas under conditions effective to produce a bottoms and an overhead comprising said secondary ethylene rich product stream;
separating said overhead into a vapor phase and a liquid phase, wherein said vapor phase comprises said secondary ethylene rich product stream; and
recovering a primary ethylene rich product stream from said bottoms.

39. The method of claim 38 wherein said conditions comprise a temperature of about −55° F.(−48° C.) or higher.

40. The method of claim 38 wherein:
said overhead consists essentially of ethylene and components of said mixed charge gas having a boiling point at least as low as ethylene; and,
said bottoms consists essentially of ethylene and components of said mixed charge gas having a boiling point at least as high as ethylene.

41. The method of claim 39 wherein
said overhead consists essentially of ethylene and components of said mixed charge gas having a boiling point at least as low as ethylene- and,
said bottoms consists essentially of ethylene and components of said mixed charge gas having a boiling point at least as high as ethylene.

42. The method of claim 41 wherein:
said overhead consists essentially of ethylene and components of said mixed charge gas having a boiling point at least as low as ethylene and,
said bottoms consists essentially of ethylene and components of said mixed charge gas having a boiling point at least as high as ethylene.

43. The method of claim 38 wherein said secondary ethylene rich product stream is produced in the absence of absorption by lean oil, and in the absence of a chill train.

44. The method of claim 41 wherein said secondary ethylene rich product stream is produced in the absence of absorption by lean oil, and in the absence of a chill train.

45. The method of claim 42 wherein said secondary ethylene rich product stream is produced in the absence of absorption by lean oil, and in the absence of a chill train.

46. In a process for producing a primary ethylene rich product stream from a pressurized mixed olefin bearing charge gas comprised of a mixture of olefins inclusive of ethylene, aliphatics, inclusive of methane, and hydrogen and carbon monoxide by fractionation in a distillation column provided with multiple distillation trays, heat is input during the operation to a reboiler located at the bottom of the column, and a portion of the effluent vapor from the overhead of the column containing methane and products lower boiling than methane is cooled, liquified, and reintroduced to the top of the column as reflux, the combination of steps comprising:
  (a) introducing the charge gas at a temperature above about −55° F. directly from an olefins generation/preparation process to the feed tray of a high temperature demethanizer fractional distillation tower whose condenser temperature is above about −55° F. under conditions sufficient to produce from the overhead of the column a vapor containing methane and products lower boiling than methane,
  (b) producing also by operation of said demethanizer a secondary ethylene rich product stream which contains virtually all of the hydrogen, carbon monoxide and methane in the charge gas along with a quantity of ethylene that is less than 50% and greater than 1% of the ethylene contained in the charge gas, and a demethanizer bottoms stream containing the balance of the material in the charge gas stream, and
  (c) introducing said demethanizer bottoms stream to a deethanizer fractional distillation tower to produce a deethanizer overhead stream containing propylene and higher boiling materials that is less than 50% of those higher boiling materials contained in the demethanizer bottoms stream, and a deethanized bottoms stream containing the balance of the material in the demethanizer bottoms stream.

47. The process of claim 46 wherein in step (c) a primary ethylene rich product stream is produced directly as the deethanizer overhead stream.

48. The process of claim 46 wherein is included, a further step (d) which comprises;
  introducing said deethanizer overhead stream from step (c) to a C2 splitter fractional distillation tower to produce a primary ethylene rich product stream as the overhead or sidestream above the feed tray containing over 50% of the ethylene in the deethanizer overhead stream along with a quantity of ethane and other higher boiling materials that is less than 50% of those higher boiling materials contained in the charge gas, and a C2 splitter bottoms stream containing the balance of the material in the deethanizer overhead stream.

49. The process of claim 46 where all or part of the secondary ethylene rich product stream in step 2(b) is introduced to a membrane device which produces a stream richer in olefins than the secondary ethylene rich product stream produced in step 2(b).

50. In a process for producing a primary ethylene rich product stream from a pressurized mixed olefin bearing charge gas comprised of a mixture of olefins, inclusive of ethylene, aliphatics, inclusive of methane, and hydrogen and carbon monoxide by fractionation in a distillation column provided with multiple distillation trays, heat is input during the operation to a reboiler located at the bottom of the column, and a portion of the effluent vapor from the overhead of the column containing methane and products lower boiling than methane is cooled, liquified, and reintroduced to the top of the column as reflux, the combination of steps comprising:
  (a) introducing the charge gas at a temperature above about 55° F., to a deethanizer fractional distillation tower to produce a deethanizer overhead stream containing over 50% of the ethane in the charge gas along with a quantity of propylene and higher boiling materials that is less than 50% of those higher boiling materials contained in the charge gas, and a deethanized bottoms stream containing the balance of the material in the charge gas,
  (b) introducing deethanizer overhead stream at a temperature above about −55° F., to the feed tray of a high temperature demethanizer fractional distillation tower whose condenser temperature is above about −55° F.,
  (c) operating said demethanizer to produce a secondary ethylene rich product stream as the overhead containing virtually all of the hydrogen, carbon monoxide and methane in the charge gas along with a quantity of ethylene that is less than 50% and greater than 1% of the ethylene contained in the deethanizer overhead stream, and a demethanized bottoms stream containing the balance of the material in the deethanizer overhead stream,
  (d) introducing said demethanizer bottoms stream to a C2 splitter fractional distillation tower to produce a primary ethylene rich product stream as the overhead or sidestream above the feed tray containing over 50% of the ethylene in the demethanizer bottoms stream along with a quantity of ethane and other higher boiling materials that is less than 50% of those higher boiling materials contained in the demethanizer bottoms stream, and a C2 splitter bottoms stream containing the balance of the material in the demethanizer bottoms stream.

51. The process of claim 50 where all or part of the secondary ethylene rich product stream produced in step (c) is introduced to a membrane device which produces a stream richer in olefins than the secondary ethylene rich product stream produced in step 60(c).

52. In a process for producing a primary ethylene rich product stream from a Pressurized mixed olefin bearing charge gas comprised of a mixture of olefins, inclusive of ethylene, aliphatics, inclusive of methane, and hydrogen and carbon monoxide by fractionation in a distillation column provided with multiple distillation trays, heat is input during the operation to a reboiler located at the bottom of the column., and a portion of the effluent vapor from the overhead of the column containing methane and products lower boiling than methane is cooled, liquified, and reintroduced to the top of the column as reflux, the combination of steps comprising:
  (a) introducing the charge gas at a temperature above about −55° F., to a high temperature demethanizer fractional distillation tower whose condenser temperature is above about −55° F.,
  (b) operating said demethanizer to produce a secondary ethylene rich product stream as the overhead containing virtually all of the hydrogen, carbon monoxide and methane in the charge gas along with a quantity of ethylene that is less than 50% and greater than 1% of the ethylene contained in the charge gas, and a demethanizer bottoms stream containing the balance of the material in the charge gas stream, (c) introducing said demethanizer bottoms stream to a C2 splitter fractional distillation tower to produce a primary ethylene rich product stream as the overhead containing over 50% of the ethylene in the deethanizer overhead stream along with a quantity of ethane and other higher boiling materials that is less than 50% of those higher boiling materials contained in the demethanizer bottoms stream, and a C2 splitter bottoms stream containing the balance of the material in the demethanizer bottoms stream.

53. The process of claim 52 where all or part of the secondary ethylene rich product stream produced in step (b) is introduced to a membrane device which produces a stream richer in olefins than the secondary ethylene rich product stream produced in step (b).

54. The method of claim 1 further comprising separating said overhead into a vapor phase and a liquid phase, wherein said vapor phase comprises said secondary ethylene rich product stream.

55. The method of claim 29 further comprising separating said overhead into a vapor phase and a liquid phase, wherein said vapor phase comprises said secondary ethylene rich product stream.

\* \* \* \* \*